US008161796B2

(12) United States Patent  
Nair et al.

(10) Patent No.: US 8,161,796 B2  
(45) Date of Patent: Apr. 24, 2012

(54) PARTICULATE MATTER SENSOR WITH AN INSULATING AIR GAP

(75) Inventors: Balakrishnan G. Nair, Sandy, UT (US); Brett Tamatea Henderson, Salt Lake City, UT (US)

(73) Assignee: EmiSense Technologies LLC, San Juan Capistrano, CA (US)

( * ) Notice: Subject to any disclaimer, the term of this patent is extended or adjusted under 35 U.S.C. 154(b) by 562 days.

(21) Appl. No.: 12/424,794

(22) Filed: Apr. 16, 2009

(65) Prior Publication Data

US 2010/0264025 A1  Oct. 21, 2010

(51) Int. Cl.
*G01N 7/00* (2006.01)
*G01N 37/00* (2006.01)

(52) U.S. Cl. ..................... 73/28.01; 73/23.33
(58) Field of Classification Search ...... 73/23.31–23.33, 73/28.01–28.02
See application file for complete search history.

(56) References Cited

U.S. PATENT DOCUMENTS

| | | | |
|---|---|---|---|
| 2,307,602 A | 1/1943 | Penney | |
| 3,826,574 A | 7/1974 | Brown, Jr. | |
| 4,004,452 A * | 1/1977 | Logothetis et al. | 73/23.32 |
| 4,121,458 A | 10/1978 | Fort | |
| 4,656,832 A | 4/1987 | Hukihisa et al. | |
| 4,713,964 A | 12/1987 | Ioannides | |
| 4,939,466 A | 7/1990 | Johnson et al. | |
| 5,008,628 A | 4/1991 | Kirgmont et al. | |
| 5,104,513 A | 4/1992 | Lee et al. | |
| 5,264,272 A | 11/1993 | Tanabe et al. | |
| 5,290,606 A | 3/1994 | Hestevik et al. | |
| 5,302,935 A | 4/1994 | Chatterjee | |
| 5,608,155 A | 3/1997 | Ye et al. | |
| 5,795,454 A | 8/1998 | Friese et al. | |
| 5,892,140 A | 4/1999 | Wood | |
| 5,922,946 A | 7/1999 | Hirota et al. | |

(Continued)

FOREIGN PATENT DOCUMENTS

| | | |
|---|---|---|
| DE | 4236711 | 5/1993 |
| DE | 19536705 | 3/1997 |
| DE | 19817402 | 9/1999 |
| JP | 60-123757 | 7/1985 |
| JP | 64-20441 | 1/1989 |

OTHER PUBLICATIONS

Young, Lee W., "International Search Report", (Aug. 15, 2008),1-3.

(Continued)

*Primary Examiner* — Hezron E Williams
*Assistant Examiner* — Nathaniel Kolb
(74) *Attorney, Agent, or Firm* — Jeffrey T. Holman

(57) ABSTRACT

An electrode assembly for a particulate matter sensor in a gas environment. The electrode assembly includes an insulating tube, a conductor, and a positioning structure. The insulating tube has an outer surface and defines an interior cavity with an interior surface. The conductor is disposed within the interior cavity of the insulating tube. The conductor is electrically coupled to an electrode at a first end of the insulating tube and includes a contact portion at a second end of the insulating tube for connection to an external conductor. The positioning structure is coupled to the conductor. The positioning structure mechanically supports the conductor at a distance from the interior surface of the insulating tube to at least partially define an air dielectric gap at approximately a heater location corresponding to a heater. The positioning structure has an outer diameter approximately equal to an inner diameter of the insulating tube and has an inner diameter approximately equal to an outer diameter of the conductor.

46 Claims, 10 Drawing Sheets

U.S. PATENT DOCUMENTS

| | | | |
|---|---|---|---|
| 5,942,190 | A | 8/1999 | Kato et al. |
| 6,076,393 | A | 6/2000 | Kato et al. |
| 6,161,421 | A | 12/2000 | Fang et al. |
| 6,214,208 | B1 | 4/2001 | Ando et al. |
| 6,557,393 | B1 | 5/2003 | Gokhfeld et al. |
| 6,634,210 | B1 | 10/2003 | Bosch et al. |
| 6,705,152 | B2 | 3/2004 | Routkevitch et al. |
| 6,763,699 | B1 | 7/2004 | Hunter et al. |
| 6,971,258 | B2 | 12/2005 | Rhodes et al. |
| 7,041,153 | B2 | 5/2006 | Totoki et al. |
| 7,063,731 | B2 | 6/2006 | Roe |
| 7,406,855 | B2 | 8/2008 | Tikkanen et al. |
| 7,891,232 | B2 * | 2/2011 | Hall ............ 73/28.01 |
| 2003/0014966 | A1 | 1/2003 | Hirota et al. |
| 2003/0121251 | A1 | 7/2003 | Kelley et al. |
| 2005/0178675 | A1 | 8/2005 | Hall |
| 2006/0016246 | A1 | 1/2006 | Rhodes et al. |
| 2007/0089399 | A1 | 4/2007 | Rhodes et al. |
| 2007/0271903 | A1 | 11/2007 | Rhodes et al. |
| 2008/0265870 | A1 | 10/2008 | Nair et al. |
| 2009/0056416 | A1 | 3/2009 | Nair et al. |
| 2010/0107737 | A1 * | 5/2010 | Krafthefer et al. ............ 73/28.01 |

OTHER PUBLICATIONS

Young, Lee W., "Written Opinion of the International Searching Authority", (Aug. 15, 2008),1-10.

Young, Lee W., "International Search Report", (Nov. 25, 2008), 1-2.

Young, Lee W., "Written Opinion of the International Searching Authority", (Nov. 25, 2008),1-6.

Hauser, "Method for Measuring Particles in Gas Flow e.g. vehicle exhaust", DE19536705, (Apr. 3, 1997),Abstract.

Hauser, "Sensor Device for Quantitative Evaluation of Particles Suspended in Gas Flow, e.g. smoke particles in diesel engine exhaust gas", DE19817402, (Sep. 30, 1999),Abstract.

Moosmueller, et al., "Time Resolved Characterization of Diesel Particulate Emissions", *Environmental Science and Technology*, vol. 35, No. 4, (2001),781-787.

Olsen, Kaj K., "International Search Report", (Feb. 13, 2004),1-5.

McCall, Eric S., "Office-Action for U.S. Appl. No. 11/039,365 sent Feb. 2, 2009", 1-6.

Hauser, "English Translation of DE-19536705", (Apr. 3, 1997),1-8.

Hauser, "English Translation of DE-19817402", (Sep. 30, 1999),1-6.

* cited by examiner

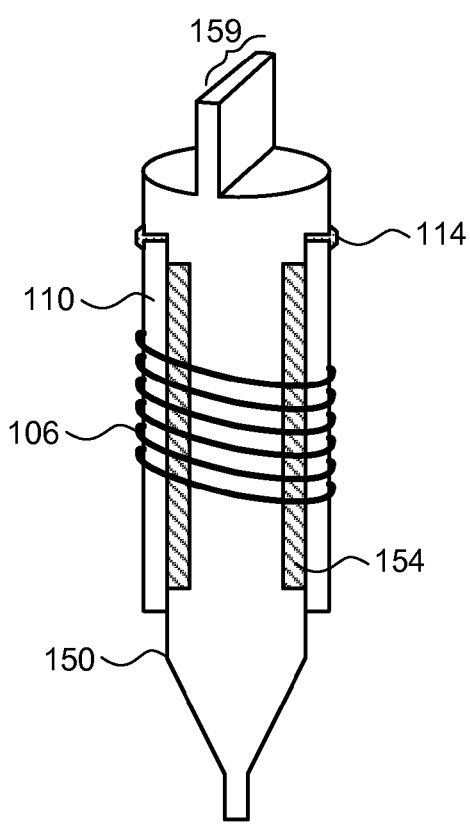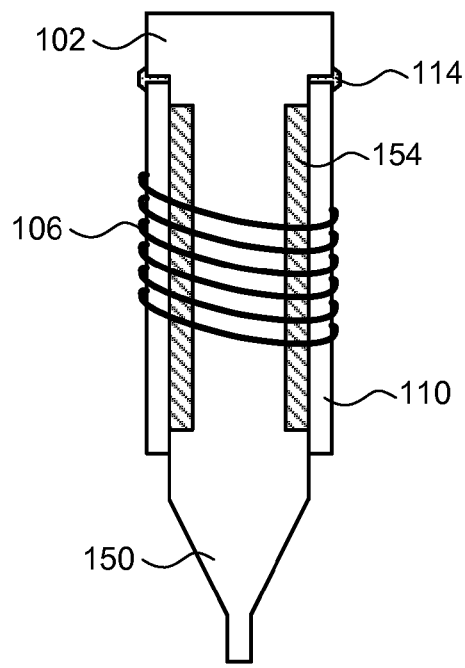
FIG. 8
FIG. 9

PARTICULATE MATTER SENSOR WITH AN INSULATING AIR GAP

BACKGROUND

Internal combustion engines (e.g., diesel engines) typically generate a gas flow that contains varying amounts of particulate matter (PM). The amount and size distribution of particulate matter in the gas flow tends to vary with engine operating conditions, such as fuel injection timing, injection pressure, or the engine speed to load relationship. Adjustment of these conditions may be useful in reducing particulate matter emissions and particulate matter sizes from the engine. Reducing particulate matter emissions from internal combustion engines is environmentally favorable. In addition, particulate matter measurements for diesel gas is useful for on-board (e.g., mounted on a vehicle) diagnostics of PM filters and reduction of emissions through combustion control.

Conventional technologies that can be used for on-board monitoring of particulate matter in gas flows include wire and ceramic-based sensors. Both types of sensors apply a high voltage to one of two electrodes and measure the current or charge on the other electrode. The electrode measurement is correlated with a specific particulate matter concentration. Wire sensors use conductive wires as the electrodes. Ceramic sensors use conductive traces, which are disposed on ceramic substrates or structures, as the electrodes. Some ceramic sensors are superior to wire sensors at least because they are easier to manufacture, cost less than wire sensors, may have more vibration resistance, and are more robust in adverse operating environments. By way of comparison, ceramic-based electrodes are more rigid than wire electrodes and, hence, vibrate less, maintain a more consistent distance between the electrodes, and produce less noise in the resulting electrical signal. However, both wire and ceramic sensors are subject to de-calibration and baseline drift of the sensor due to accumulation of soot (i.e., particulate matter) on and between the electrodes. Additionally, conventional wire sensors have a limited area where the electrodes face each other, so the resulting sensor signals may be relatively small.

For ceramic sensors, electrode heaters can be integrated into the ceramic sensor structure to burn off soot at the electrodes. However, the electrode heaters can significantly increase the temperature of the electrodes and the electrical leads connecting the electrodes to the electronics module. Increasing the temperature of the electrodes at the same time that a high voltage is applied to the electrodes (e.g., one of the electrodes) can result in electrical leakage through the ceramic materials because the increased temperature decreases the insulating properties of the ceramic materials. This type of electrical leakage can impair the accuracy of the sensor measurements.

SUMMARY

Embodiments of an apparatus are described. In one embodiment, the apparatus is an electrode assembly for a particulate matter sensor in a gas environment. The electrode assembly may include an insulating tube, a conductor, and a positioning structure. The insulating tube has an outer surface and defines an interior cavity with an interior surface. In one embodiment, the conductor is disposed within the interior cavity of the insulating tube. The conductor may be electrically coupled to an electrode at the first end of the insulating tube. The conductor may include a contact portion at the second end of the insulating tube for connecting to an external conduct. The positioning structure may be coupled the conductor. In one embodiment, the positioning structure mechanically supports the conductor at a distance from the interior surface of the insulating tube to at least partially define an air dielectric gap at approximately a heater location corresponding to a heater. The positioning structure may have an outer diameter approximately equal to the inner diameter of the insulating tube and an inner diameter approximately equal to the outer diameter of the conductor.

Another embodiment of an electrode assembly is also described. In this embodiment, the electrode assembly includes an insulating tube and a conductive pin. The insulating tube has an outer surface and defines an interior cavity with an interior surface. The conductive pin may be disposed within the interior cavity of the insulating tube. In this embodiment, the conductive pin includes an electrode portion, a contact portion, and an intermediate portion. The electrode portion may be at a first end of the insulating tube. The contact portion may be at a second end of the insulating tube for connection to an external conductor. The intermediate portion is between the electrode portion and the contact portion. The intermediate portion may have dimensions smaller than the interior cavity of the insulating tube to at least partially define an air dielectric gap between the intermediate portion and the interior surface of the insulating tube.

Another embodiment of an electrode assembly is also described. In this embodiment, the electrode assembly includes an insulating tube, a conductive wire, and mechanical plugs. The insulating tube has an outer surface and defines an interior cavity with an interior surface. The conductive wire may be disposed within the interior cavity of the insulating tube. In this embodiment, the conductive wire is electrically coupled to an electrode at a first end of the insulating tube. The conductive wire may include a contact portion at a second end of the insulating tube for connection to an external conductor. In this embodiment, the mechanical plugs are coupled to the conductive wire within the insulating tube. In this embodiment, the mechanical plugs mechanically support an intermediate portion of the conductive wire at a distance from the interior surface of the insulating tube to at least partially define an air dielectric gap between the conductive wire and the interior surface of the insulating tube. Other embodiments of the apparatus are also described.

Embodiments of a sensor for use in a gas environment are also described. In one embodiment, the sensor includes an insulating structure, and electrode, a conductor, and a heater. The insulating structure may be any type of insulating material (e.g., ceramic, glass, etc.) having any type of geometrical shape (e.g., tubular, planar, etc.) and/or size suitable for use in a gas environment. The electrode in one embodiment is structurally coupled to the insulating structure. The electrode conducts an electrical signal that is dependent on a gas flow within the gas environment. The conductor is electrically coupled to the electrode. The conductor conveys the electrical signal from the electrode to an external conductor. The heater may be disposed relative to the insulating structure. In this embodiment, the heater heats at least a portion of the insulating structure to burn off an accumulation of particulate matter from the insulating structure. The heater may be positioned relative to the conductor to define an air dielectric gap between the heater and the conductor. The air dielectric gap prevents electromagnetic interference originating at the heater from substantially disrupting the electrical signal on the conductor. In some embodiments, the air dielectric gap is an air gap distance of at least about 15 microns between the heater and the conductor. In other embodiments, the air gap distance is at least about 100 microns. In some embodiments, the air dielectric gap is partially or completely located between the heater and the insulating structure, in which case the heater may be physically separated from the insulting structure so that there is no direct physical contact between the heater and the insulating structure. In other embodiments, the air dielectric gap is partially or completely between the insulating structure and the conductor, in which case the heater may be in direct physical contact with at least a portion of the insulating structure. In other embodiments, the air dielectric gap is a combination of gaps, for example, between the heater and the insulating structure and between the insulating structure and the conductor. Other embodiments of the sensor are also described.

Embodiments of a system are also described. In one embodiment, the system is a system for detecting particulate matter. The system may include a sensor assembly and an electronic controller. The sensor assembly detects the particulate matter in a gas environment. In this embodiment, the sensor assembly includes a pair of insulating tubes, conductors, and positioning structures. A conductor may be disposed within an interior cavity of each insulating tube. Each conductor is electrically coupled to an electrode at a first end of the corresponding insulating tube. Each conductor may include a contact portion at a second end of the corresponding insulating tube for connection to an external conduct. In this embodiment, at least a portion of each conductor is offset from the interior surface of the insulating tube by an air dielectric gap at approximately a heater location corresponding to a heater. A positioning structure may be coupled to each conductor. The positioning structure mechanically supports the corresponding conductor at a distance from the interior surface of the corresponding insulating tube to at least partially define the air dielectric gap around the corresponding conductor. The electronic controller determines an amount of particulate matter within the gas environment. Other embodiments of the system are also described.

Embodiments of a method are also described. In one embodiment, the method is a method for making an electrode assembly for a particulate matter sensor. In this embodiment, the method includes disposing a conductive pin within an interior cavity of an insulating tube. The conductive pin may include an electrode portion, a contact portion at a first end of the insulating tube, a contact portion at the second end of the insulating tube, and an intermediate portion between the electrode portion and the contact portion. The electrode portion may be coupled to an electrode at the first end of the insulating tube. The contact portion at the second end of the insulating tube connects to an external conductor. The intermediate portion may have dimensions smaller than the interior cavity of the insulating tube to at least partially define an air dielectric gap between the intermediate portion and an interior surface of the insulating tube. The method may also include disposing a heater outside of the insulating tube at approximately a location of the air dielectric gap. The heater applies heat to burn off particulate matter from the insulating tube.

In another embodiment, the method includes disposing a conductive wire within an interior cavity of an insulating tube. The conductive wire may be electrically coupled to an electrode at a first end of the insulating tube. The conductive wire in this embodiment includes a contact portion at a second end of the insulating tube for connection to an external conductor. The method may include disposing mechanical plugs coupled to the conductive wire within the insulating tube. The mechanical plugs mechanically support an intermediate portion of the conductive wire at a distance from an interior surface of the insulating tube to at least partially define an air dielectric gap between the conductive wire and the interior surface of the insulating tube. The method may also include disposing a heater outside of the insulating tube at approximately a location of the air dielectric gap. The heater generates sufficient heat to burn off particulate matter from the insulating tube, either continuously or intermittently, depending on the application. Other embodiments of the method are also described.

Embodiments of a sensor for use in a gas environment are also described. In one embodiment, the sensor includes an insulating structure, and electrode, a conductor, and a heater. The insulating structure may be any type of insulating material (e.g., ceramic, glass, etc.) having any type of geometrical shape (e.g., tubular, planar, etc.) and/or size suitable for use in a gas environment. The electrode in one embodiment is structurally coupled to the insulating structure. The electrode conducts an electrical signal that is dependent on a gas flow within the gas environment. The conductor is electrically coupled to the electrode. The conductor conveys the electrical signal from the electrode to an external conductor. The heater maybe disposed relative to the insulating structure. In this embodiment, the heater heats at least a portion of the insulating structure to burn off an accumulation of particulate matter from the insulating structure. The heater maybe positioned relative to the conductor to define an air dielectric gap between the heater and the conductor. The air dielectric gap prevents electromagnetic interference originating at the heater from substantially disrupting the electrical signal on the conductor. In some embodiments, the air dielectric gap is an air gap distance of at least about 15 microns between the heater and the conductor. In other embodiments, the air gap distance is at least about 100 microns. In some embodiments, the air dielectric gap is partially or completely located between the heater and the insulating structure, in which case the heater may be physically separated from the insulting structure so that there is no direct physical contact between the heater and the insulating structure. In other embodiments, the air dielectric gap is partially or completely between the insulating structure and the conductor, in which case the heater may be in direct physical contact with at least a portion of the insulating structure. In other embodiments, the air dielectric gap is a combination of gaps, for example, between the heater and the insulating structure and between the insulating structure and the conductor. Other embodiments of the sensor are also described.

Some embodiments may combine two or more of the various structures described herein. Other embodiments of the particulate matter sensor and the means for substantially preventing electrical leakage through the insulating material are also described. Other aspects and advantages of embodiments of the present invention will become apparent from the following detailed description, taken in conjunction with the accompanying drawings, illustrated by way of example of the principles of the invention.

BRIEF DESCRIPTION OF THE DRAWINGS

FIG. 8 depicts a schematic diagram of another embodiment of the electrode assembly of FIG. 7.

FIG. 9 depicts a schematic diagram of another embodiment of the electrode assembly of FIG. 7.

Throughout the description, similar reference numbers may be used to identify similar elements.

DETAILED DESCRIPTION

Figure 1:
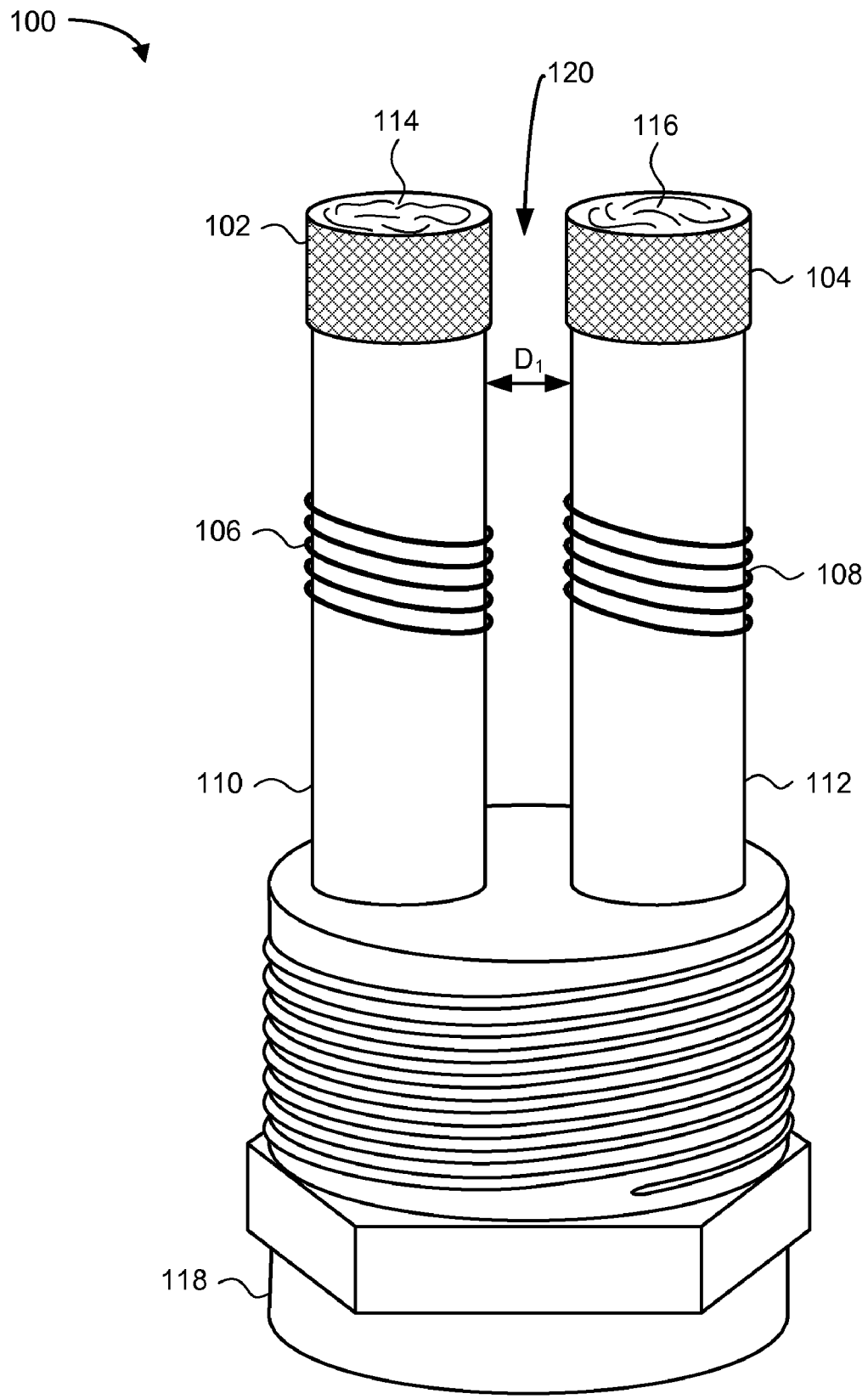
FIG. 1 depicts a schematic diagram of one embodiment of a particulate matter sensor.

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

While many embodiments of a particulate matter sensor are described herein, at least some of the described embodiments detect particulate matter in a gas environment or a gas stream. The sensor includes two electrodes on a pair of insulating tubes. In some embodiments, the insulating tubes are ceramic tubes, although the tubes may be made of other insulating materials such as glass. For convenience, the present description refers to ceramic tubes in many locations; however, these references to ceramic tubes are intended to refer to any suitable type of insulating tubes.

The electrodes are oriented to have at least part of the surfaces of each electrode face each other. An air gap between the two electrodes allows gas to flow between the two electrodes. In some embodiments, the first electrode is a detection electrode. The detection electrode is disposed on the first ceramic tube. The second electrode is a bias electrode and is disposed on the second ceramic tube. The bias electrode has an applied voltage, also referred to as a bias voltage. As the particulate matter in the gas stream passes between the bias and detection electrodes, a charge builds up or a current flows on the detection electrode. An electronic controller measures an electrical characteristic in the form of a charge, current, or voltage, and determines an amount of particulate matter in the gas.

Additionally, as gas passes through the sensor, particulate matter may build up on the surfaces of the sensor. Deposits on the detection and bias electrodes can distort particulate matter measurements, or cause electrical shorts between the electrodes. In some embodiments, each ceramic tube of the sensor includes a heater located on the tube. A wire heater may be wrapped around the ceramic tube. Other embodiments include a heater printed, disposed, or chemically applied to the ceramic tube. In some embodiments, the heater is at least partially recessed in a groove of the ceramic tube. The heater is configured to generate heat sufficient to burn off the particulate matter deposits on the surfaces of the rigid tube. In particular, the heaters may burn off particulate matter deposits on the detection and bias electrodes.

Also, in some embodiments, by locating the electrodes on two separate ceramic tubes, typical problems relating to electrical leakage through intermediate ceramic layers can be avoided. While conventional ceramic sensors can exhibit electrical leakage at high voltages and/or high operating temperatures (due to decreased electrical insulating properties of the intermediate ceramic layer), embodiments of the particulate matter sensor described herein do not exhibit electrical leakage between the electrodes. In other words, embodiments with the electrodes mounted on separate structures (e.g., rigid tubes) have reduced charge leakage which results in reduced signal distortion, compared with conventional ceramic particulate matter sensors made from a single stack of ceramic and conductive layers.

FIG. 1 depicts a schematic diagram of one embodiment of a particulate matter sensor 100. The illustrated particulate matter sensor 100 includes a detection electrode 102, a bias electrode 104, a first wire heater 106, a second wire heater 108, a first ceramic tube 110, a second ceramic tube 112, a detection electrode braze 114, a bias electrode braze 116, and a sensor base 118. Although the particulate matter sensor 100 is shown and described with certain components and functionality, other embodiments of the particulate matter sensor 100 may include fewer or more components to implement less or more functionality.

In some embodiments, the first ceramic tube 110 is made of non-conductive ceramic. For example, the first ceramic tube 110 may be made of alumina ($Al_2O_3$), magnesia (MgO), magnesium aluminate spinel ($MgAl_2O_4$), or other types of spinels. Other embodiments may use other types of ceramics and/or non-conductive materials. In one embodiment, the first ceramic tube 110 has a substantially cylindrical geometry. The first ceramic tube 110 has an outer diameter that is substantially constant along the length of the first ceramic tube 110. In some embodiments, the first ceramic tube 110 has an inner diameter to retain the structural stability of the first ceramic tube 110. In one embodiment, the outer diameter of the first ceramic tube 110 is between about 6 to about 7 mm (approximately 0.25 inch). In other embodiments, the outer diameter of the first ceramic tube 110 is between about 5 to about 10 mm. In some embodiments, the wall thickness of the first ceramic tube 110 is about 1 mm (approximately 30 to 40 thousandths of an inch). In other embodiments, the wall thickness of the first ceramic tube 110 is about 0.5 to about 2 mm. The inner diameter of the first ceramic tube 110 depends on the outer diameter and the wall thickness of the first ceramic tube 110. However, at least some embodiments of the first ceramic tube 110 have an inner diameter that is sufficiently large to at least partially define an interior cavity within the first ceramic tube 110. Other embodiments may use other dimensions for the inner or outer diameters, or the wall thickness, of the first ceramic tube 110.

The first ceramic tube 110 is aligned parallel to the second ceramic tube 112. The second ceramic tube 112 is substantially similar to the first ceramic tube 110. In some embodiments, the first and second ceramic tubes 110 and 112 are formed of the same ceramic materials. In other embodiments, the first and second ceramic tubes 110 and 112 are formed of different ceramic or non-conductive materials. The first and second ceramic tubes 110 and 112 define an air gap 120. The air gap 120 allows air, or gas, to flow between the first and second ceramic tubes 110 and 112. The air gap 120 separates the first and second ceramic tubes 110 and 112, as well as the corresponding detection and bias electrodes 102 and 104, by a distance $D_1$.

The detection electrode 102 is disposed on the outer surface of the first ceramic tube 110. The detection electrode 102 is made of a conductive material. The detection electrode 102 may include, for example, a metallic foil made of platinum, gold, tungsten, nickel, or a mullite-based material. Other embodiments may use other types of conductive materials. In some embodiments, the detection electrode 102 is painted onto an outer surface of the first ceramic tube 110. In another embodiment, the detection electrode 102 is printed onto the outer surface of the first ceramic tube 110. In other embodiments, the detection electrode 102 is chemically deposited onto the outer surface of the first ceramic tube 110.

The bias electrode 104 is substantially similar in structure and material to the detection electrode 102. In particular, the bias electrode 104 is disposed on an outer surface of the second ceramic tube 112. In the illustrated embodiment, the detection and bias electrodes 102 and 104 circumscribe the corresponding first and second ceramic tubes 110 and 112. Alternatively, the detection and bias electrodes 102 and 104 may cover only a portion of the circumference, or perimeter, of the first and second ceramic tubes 102 and 104. In some embodiments, the detection and bias electrodes 102 and 104 may be between about 1.0 to about 2.0 square cm. In another embodiment, the surface area of each of the electrodes 102 and 104 is between about 0.5 to about 4.0 square cm. Other embodiments may have electrodes 102 and 104 with smaller or larger surface areas.

In some embodiments, the bias electrode 104 is biased and generates an electric field. In one embodiment, a bias voltage is applied to the bias electrode 104. The bias voltage of the bias electrode 104 may be, for example, between about 1 to about 10,000 Volts. Alternatively, the bias voltage may be between about 500 to about 5,000 Volts. Other embodiments may use other bias voltages. By biasing the bias electrode 104, the particulate matter passing in the gas stream between the bias electrode 104 and the detection electrode 102 affects a charge or current on the detection electrode 102. The charge or current (or voltage) on the detection electrode 102 can be correlated with a particulate matter concentration within the gas stream. In this way, the detection electrode 102 facilitates detection of the particulate matter in the gas stream.

The detection and bias electrodes 102 and 104 include detection and bias electrode brazes 114 and 116 applied to the end of the first and second ceramic tubes 110 and 112, respectively. The detection and bias electrode brazes 114 and 116 are applied through a thermal process. The electrode brazes 114 and 116 may function to provide or increase the electrically conductive surface area of the detection and bias electrodes 102 and 104. In some embodiments, the electrode brazes 114 and 116 electrically connect the electrodes 102 and 104 to internal components (not shown) within the corresponding ceramic tubes 110 and 112. Other embodiments may implement other configurations for the detection and bias electrode brazes 114 and 116.

In order to measure the charge on the detection electrode 102, some embodiments of the sensor 100 include a charge amplifier (not shown) coupled to the detection electrode 102. The charge amplifier may be calibrated to measure an accumulated electric charge on the detection electrode 102 as particulate matter flows within the gas stream between the detection and bias electrodes 102 and 104. The electric charge that accumulates on the detection electrode 102 varies with the mass concentration of particulate matter in the gas stream. Thus, the charge amplifier may generate an output voltage corresponding to the measured accumulated electric charge. In general, the charge amplifier obtains a voltage proportional to the charge and yields a low output impedance. Hence, the charge amplifier also may be referred to as a charge-to-voltage converter.

Alternatively, in some embodiments, current flow on the detection electrode 102 may be measured in order to determine an amount of particulate matter in the gas stream. In another embodiment, voltage or another electrical parameter may be measured to determine the amount of particulate matter in the gas stream.

The first and second heaters 106 and 108 are located on the outer surfaces of the first and second ceramic tubes 110 and 112 respectively. In the illustrated embodiment, the first and second heaters 106 and 108 are resistive wires coiled around the first and second ceramic tubes 110 and 112 respectively. The first and second heaters 106 and 108 generate heat to burn off particulate matter that collects on each electrode assembly of the particulate matter sensor 100. In some embodiments, the heaters 106 and 108 are electrical resistance heaters. Other embodiments may use other types or physical configurations of heaters to generate heat and burn off particulate matter deposits.

Figure 2:
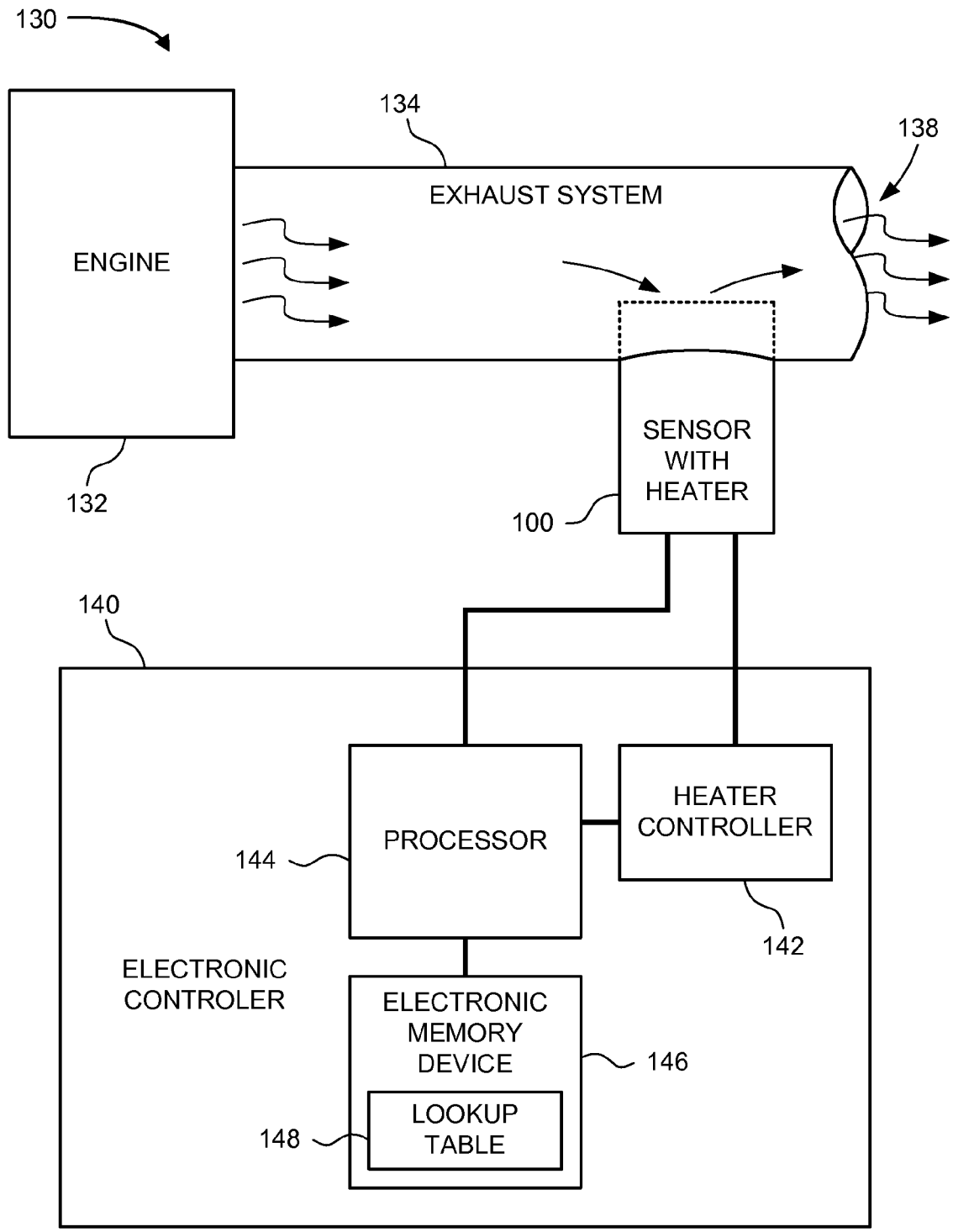
FIG. 2 depicts a block diagram of one embodiment of a particulate matter detection system which uses the particulate matter sensor of FIG. 1.

FIG. 2 depicts a schematic block diagram of one embodiment of a particulate matter detection system 130 which uses the particulate matter sensor 100 of FIG. 1. The illustrated embodiment includes the particulate matter sensor 100, an engine 132, and a gas system 134. The engine 132 produces gas which moves through the gas system 134. The gas system 134 facilitates flow of the gas gases to a gas outlet 138. The sensor 100 is at least partially inserted into the gas system 134 to detect particulate matter in the gas stream. As the gas in the gas system 134 passes over and through the sensor 100, the sensor 100 detects the particulate matter within the gas by measuring changes in the electrical characteristics at the sensor 100, as described above.

The particulate matter detection system 130 also includes an electronic controller 140. The electronic controller 140 includes a heater controller 142, a processor 144, and an electronic memory device 146. The sensor 100 relays the sensor signal to the processor 144 of the electronic controller 140. In some embodiments, the processor 144 analyzes the sensor signal from the sensor 100. If the sensor signal is corrupted, the processor 144 sends a control signal to the heater controller 142. The heater controller 142 activates one or more heaters on the sensor 100 to burn off particulate matter deposits that might corrupt the sensor signal from the sensor 100. In some embodiments, the processor 144 sends the control signal to the heater controller 142 to activate the heater on the sensor 100 according to a timing scheme or on some other substantially continuous or non-continuous basis.

If the sensor signal from the sensor 100 is not corrupt, the processor 144 compares the sensor signal with data stored in a lookup table 148 on the electronic memory device 146 to determine one or more qualities of the gas in the gas system 134. For example, the processor 144 may determine an amount of particulate matter in the gas stream. The processor 144 also may compare the sensor signal from the sensor 100 with data from the lookup table 148 to estimate, for example, a mass concentration of particulate matter in the gas stream. In other embodiments, the electronic controller 140 facilitates detection of one or more other qualities of the gas in the gas system 134.

Some embodiments of the particulate measurement system 130 also may include one or more emissions control elements (not shown) to emit neutralizing chemicals into the gas system 134 either before or after the sensor 100. It should also be noted that embodiments of the sensor 100 may be tolerant of fluctuations of certain gaseous constituents in a gas environment.

It should also be noted that the sensor 100 may be used, in some embodiments, to determine a failure in another component of the particulate matter detection system 130. For example, the sensor element 100 may be used to determine a failure of a particulate matter filter (not shown) within the gas system 134. In one embodiment, a failure within the particulate matter detection system 130 may be detected by an elevated signal generated by the sensor 100. In some embodiments, the particulate matter detection system 130 includes an alarm to indicate a detected failure of the sensor 100 or other component of the particulate matter detection system 130. In some embodiments, the sensor 100 also could be coupled to another sensor or detector such as a mass flow meter.

Figure 3:
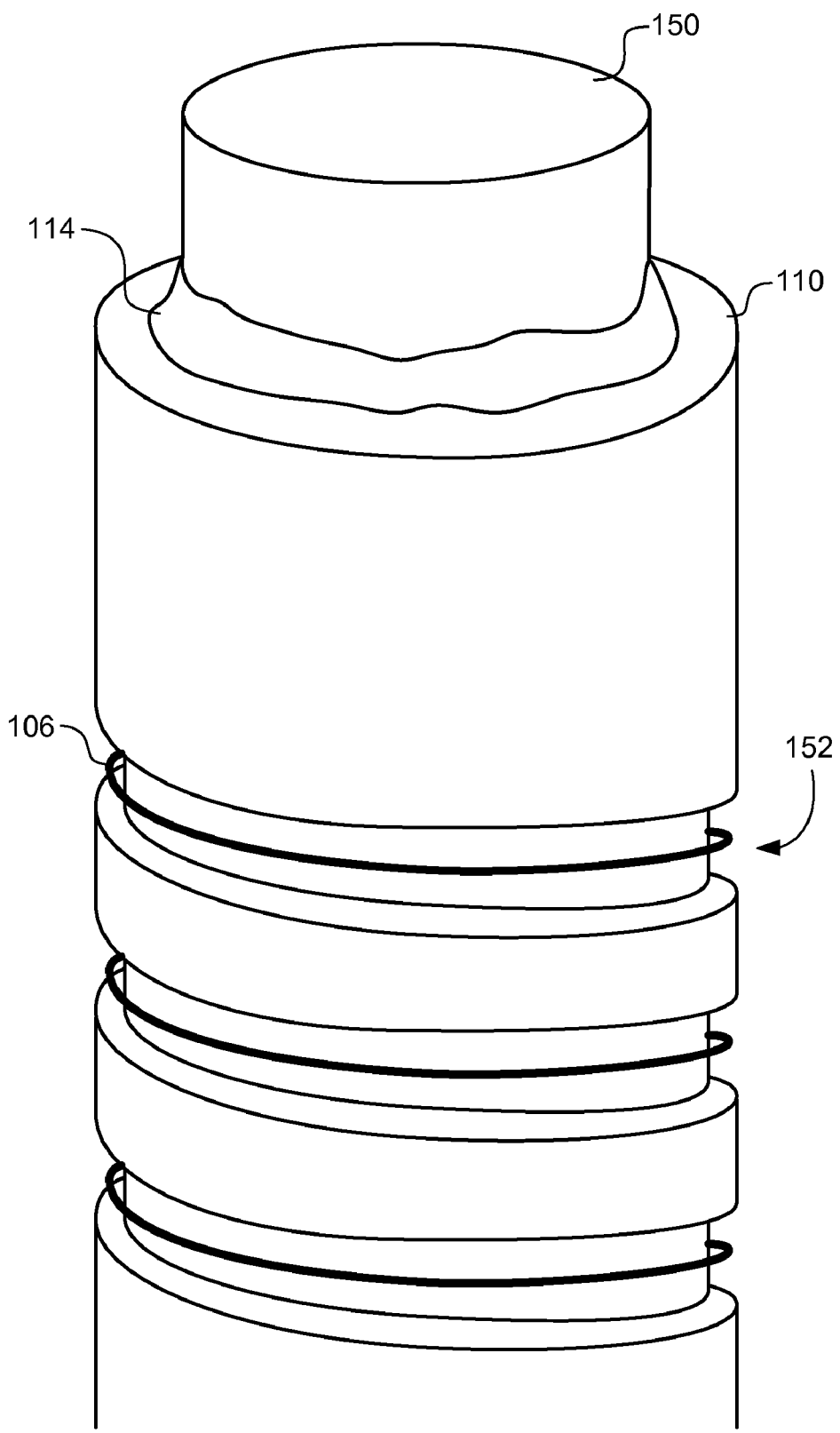
FIG. 3 depicts a schematic diagram of one embodiment of an electrode assembly with a recessed heater.

FIG. 3 depicts a schematic diagram of one embodiment of an electrode assembly with a recessed heater 106. The heater 106 is at least partially recessed within a groove 152 on the outer surface of the first ceramic tube 110. In one embodiment, the heater 108 and the second ceramic tube 112 are similar in structure and function to the heater 106 and the first ceramic tube 110. Alternatively, the groove 152 may have another geometry, for example, to enclose the heater 106.

In the illustrated embodiment, a cylindrical electrode 150 protrudes from the end of the ceramic tube 110. In some embodiments, the cylindrical electrode 150 is part of a conductive pin (described in more detail below) located inside the internal cavity of the ceramic tube 110.

FIG. 3 also illustrates the braze 114 applied to the junction of the ceramic tube 110 and the cylindrical electrode 150. In some embodiments, the braze 114 is a high-temperature metallic braze. The braze 114 may provide additional structural integrity. The braze 114 may be electrically conductive or insulating.

In one embodiment, the heater 106 maintains specific operating temperatures for the corresponding ceramic tube 110 and, in particular, the corresponding cylindrical electrode 150. The heater 106 may operate continuously, periodically, or on some other non-continuous basis. In one embodiment, the heater element 106 operates within a temperature range of approximately 200° C. or higher to burn off particulate matter from the ceramic tube 110, which may include burning off particulate matter accumulated on the electrode 150. In some embodiments, the heater element 106 operates within a temperature range of approximately 400° C. or higher. Other embodiments of the heater element 106 may operate at other temperatures.

Figure 4:
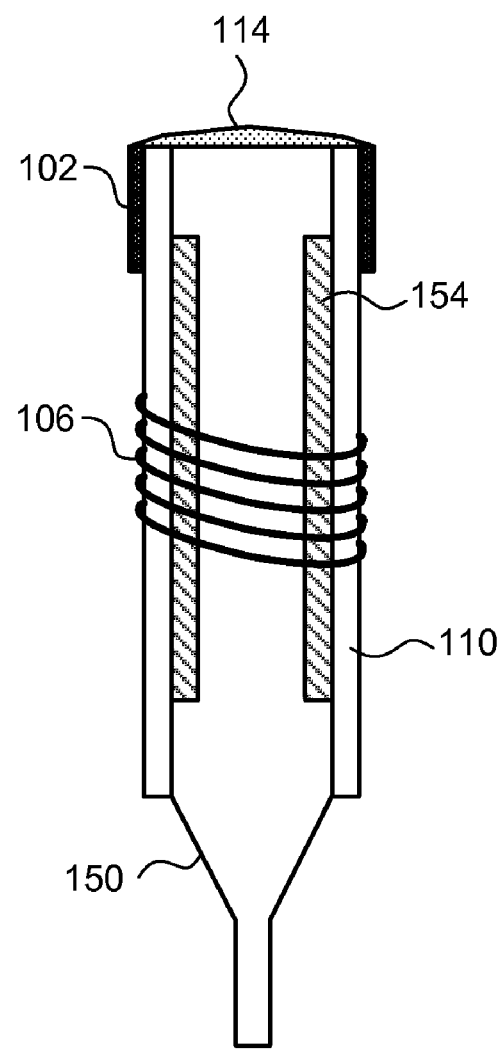
FIG. 4 depicts a schematic diagram of one embodiment of an electrode assembly which uses a conductive pin for electrical contact with the electrode.

FIG. 4 depicts a schematic diagram of one embodiment of an electrode assembly which uses a conductive pin 150 for electrical contact with the electrode 102. The illustrated embodiment includes the electrode 102, the heater 106, the ceramic tube 110, the braze 114, and a conductive pin 150. The electrode 102 is disposed on the ceramic tube 110. The ceramic tube 110 contains the conductive pin 150. The conductive pin 150 forms an electrical connection with the electrode 102 via the braze 114 that is applied at the top of the conductive pin 150 and the tube 110. The end of the conductive pin 150 that connects to the electrode 102 is designated as an electrode portion. The other end of the conductive pin 150 is designated as a contact portion. The contact portion of the conductive pin 150 facilitates electrical communication with an external conductor, for example, to the electronic controller 140 of FIG. 2.

The geometry of the pin 150 forms an air dielectric gap 154. In particular, the conductive pin 150 includes positioning structures (e.g., the wider end portions which make contact with the interior surface of the ceramic tube 110) to maintain an intermediate portion of the conductive pin 150 at a distance from the interior surface of the ceramic tube 110. The air dielectric gap 154 is formed at the intermediate portion of the conductive pin 150 where the diameter of the conductive pin 150 is less than the inner diameter of the ceramic tube 110. The thickness of the air dielectric gap 154 is half the difference between the inner diameter of the ceramic tube 110 and the diameter of the conductive pin 150 at the intermediate portion.

The air dielectric gap 154 is at least partially aligned with the heater 106. As explained above, the heater 106 generates heat to burn off particulate matter deposits that accumulate on the electrode assembly. However, as the temperature of the ceramic increases, electrical leakage can occur through the ceramic materials because the increased temperature decreases the insulating properties of the ceramic materials. The air dielectric gap 154 eliminates or substantially reduces the electrical leakage from the heater 106 to the conductive pin 150 by forming an intermediate dielectric layer. In one embodiment, the air dielectric layer substantially reduces the electrical leakage so that the signal from the electrode 102 is not corrupted by noise from the voltage or current on the heater 106.

Figure 5:
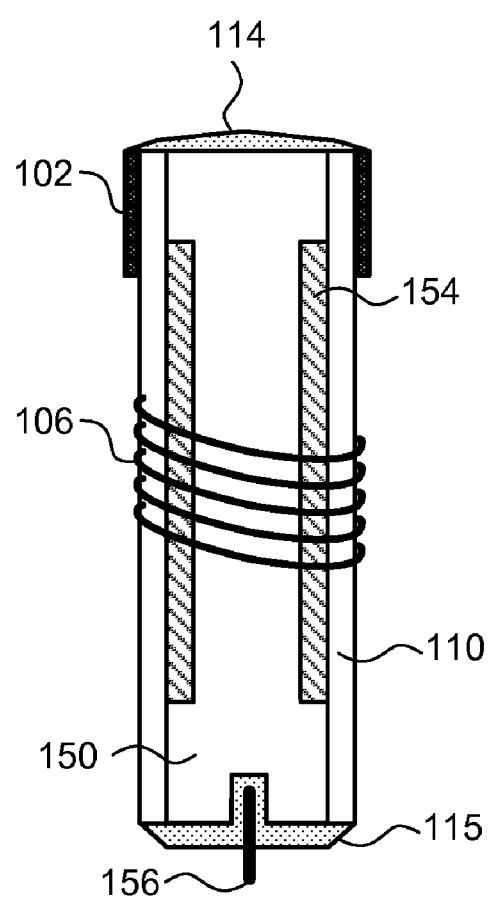
FIG. 5 depicts a schematic diagram of another embodiment of an electrode assembly with a different geometry for the connection portion of the conductive pin.

FIG. 5 depicts a schematic diagram of another embodiment of an electrode assembly with a different geometry for the connection portion of the conductive pin 150. Otherwise, the electrode assembly of FIG. 5 includes all of the same components as described with reference to FIG. 4. In one aspect, the contact portion of the conductive pin 150 is different because the contact portion does not protrude from the interior cavity of the ceramic tube 110. Rather, the contact portion includes a recess for insertion of an external wire 156. The connector wire 156 facilitates an electrical connection of the electrode assembly, for example, to the electronic controller 140 of FIG. 2. In some embodiments, the external wire 156 is mechanically supported, or held in place, by a braze 115 applied to the conductive pin 150 and the external wire 156. Additionally, the braze 115 may be conductive to facilitate electrical transmissions from the conductive pin 150 to the external wire 156. Also, the braze 115 may be applied to the ceramic tube 110 to mechanically support the conductive pin 150 and maintain the conductive pin 150 within the ceramic tube 110.

Figure 6:
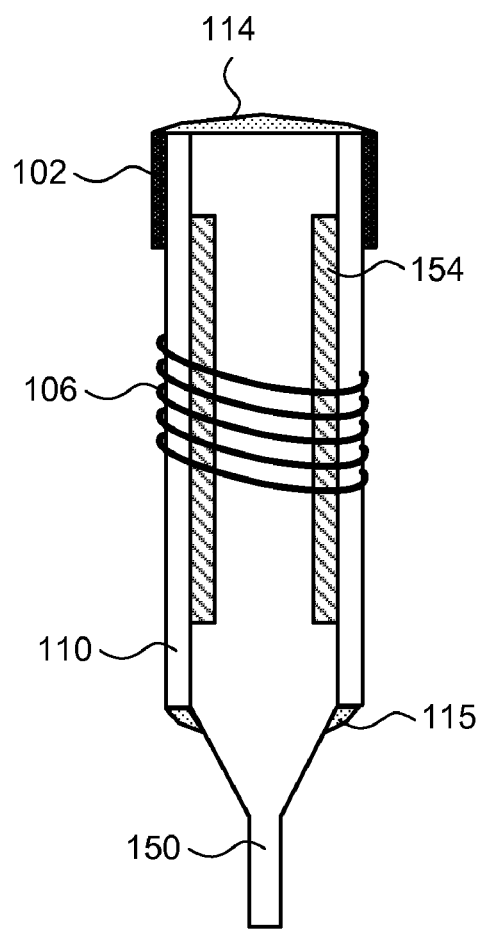
FIG. 6 depicts a schematic diagram of another embodiment of the electrode assembly of FIG. 4.

FIG. 6 depicts a schematic diagram of another embodiment of the electrode assembly of FIG. 4. The electrode assembly of FIG. 6 includes all of the same components as described above with reference to FIG. 4. Additionally, the electrode assembly of FIG. 6 includes a braze 115 applied to the contact portion of the conductive pin 150 and the ceramic tube 110. The braze 115 may provide added structural integrity to mechanically support the conductive pin 150 and maintain the conductive pin 150 within the ceramic tube 110. The braze 115 also may at least partially seal the space between the conductive pin 150 and the ceramic tube 110 to reduce the amount of particulate matter that might enter the air dielectric gap 154.

Figure 7:
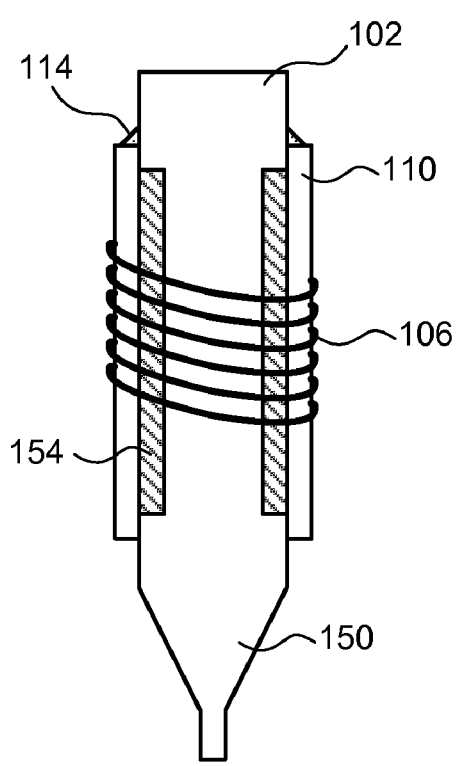
FIG. 7 depicts a schematic diagram of another embodiment of an electrode assembly with a different geometry for the electrode portion of the conductive pin.

FIG. 7 depicts a schematic diagram of another embodiment of an electrode assembly with a different geometry for the electrode portion of the conductive pin 150. Otherwise, the electrode assembly of FIG. 7 includes all of the same components as described above with reference to FIG. 4. In one aspect, the electrode portion of the conductive pin 150 is different because the electrode portion extends out of the ceramic tube 110 to at least partially form the electrode. Hence, in some embodiments, the electrode 102 (e.g., shown in FIG. 6) may be omitted from the surface of the ceramic tube 110. In the illustrated embodiment, the conductive pin 150 functions as the electrode in the electrode assembly, thus eliminating the need for a separate electrode structure on the outer surface of the ceramic tube 110. In some embodiments, the electrode portion of the conductive pin 150 is mechanically secured within the ceramic tube 110 by the braze 114.

FIG. 8 depicts a schematic diagram of another embodiment of the electrode assembly of FIG. 7. The electrode assembly of FIG. 8 includes all of the same components as described above with reference to FIG. 7. However, in the sensor assembly of FIG. 8, the conductive pin 150 has a modified geometry to allow the conductive pin 150 to extend diametrically outward to the edge of the ceramic tube 110, or beyond. Hence, the electrode portion of the conductive pin 150 functions as the electrode of the electrode assembly. In the illustrated embodiment, the electrode portion of the conductive pin 150 has a diameter approximately equal to the outer diameter of the ceramic tube 110. Other embodiments may have other diameters. The increased diameter provides a larger surface area, which may be more effective to increase signal strength and accuracy. Additionally, the electrode portion of the conductive pin 150 is mechanically coupled and sealed to the ceramic tube with a high temperature braze 114. In this way, the high temperature braze 114 may increase the resiliency of the electrode assembly. The braze 114 also may reduce the amount of particulate matter that enters the air dielectric gap 154.

FIG. 9 depicts a schematic diagram of another embodiment of the electrode assembly of FIG. 7. The electrode assembly of FIG. 9 includes all the components described above with reference to FIG. 7. However, the sensor assembly of FIG. 9 also includes a flat portion 159 at the electrode portion of the conductive pin 150. The flat portion protrudes above the ceramic tube 110 and may provide increased electrode surface area to improve detection accuracy in the signal corresponding to the particulate matter in a gas stream. The flat portion 159 may also facilitate further penetration of the electrode surface into the gas stream. Other embodiments may use a different geometry for the electrode portion of the conductive pin 150.

Figure 10:
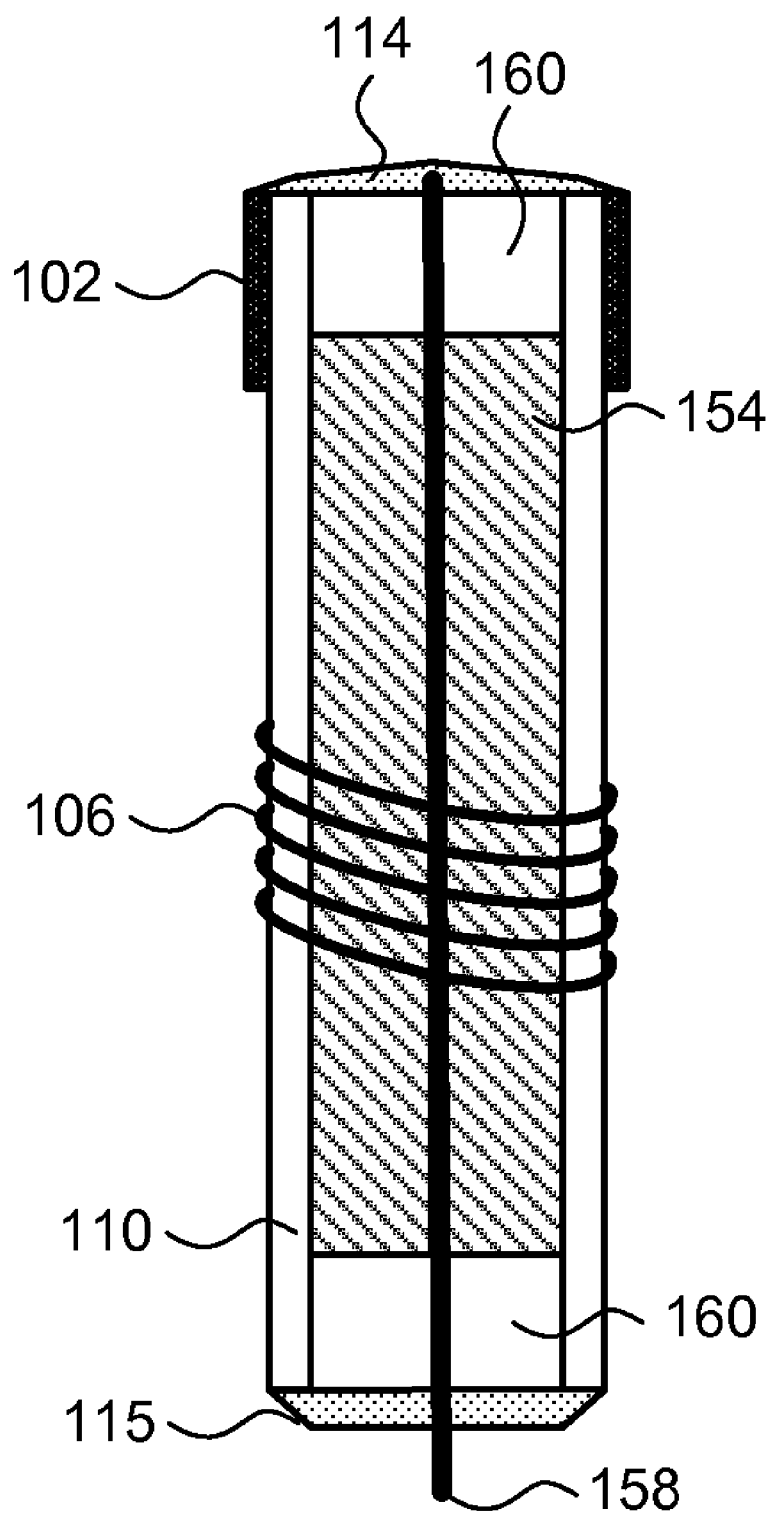
FIG. 10 depicts a schematic diagram of another embodiment of an electrode assembly which uses a conductive wire instead of a conductive pin.

FIG. 10 depicts a schematic diagram of another embodiment of an electrode assembly which uses a conductive wire 158 instead of a conductive pin 150. The electrode assembly of FIG. 10 includes the ceramic tube 110, the electrode 102, the heater 106, the electrode braze 114, the conductor braze 115, the conductive wire 158, and two mechanical plugs 158. In the depicted embodiment, the conductive wire 158 is supported by the mechanical plugs 158, which function as positioning structures to hold the conductive wire 158 in place within the ceramic tube 110. The In particular, the mechanical plugs 160 hold the conductive wire 158 so that the conductive wire 158 is located a distance from the interior surface of the ceramic tube 110. The distance between the wire conductor 156 and the interior surface of the ceramic tube 110 forms an air dielectric gap 154. The electrode braze 114 electrically connects the conductor wire 156 to the electrode 102. The electrode braze 114 also may structurally support the conductive wire 158 and/or the top mechanical plug 160 to improve the structural integrity of the electrode assembly. Similarly, the conductor braze 115 may structurally support the conductive wire 158 and/or the bottom mechanical plug 160 within the ceramic tube 110.

Figure 11:
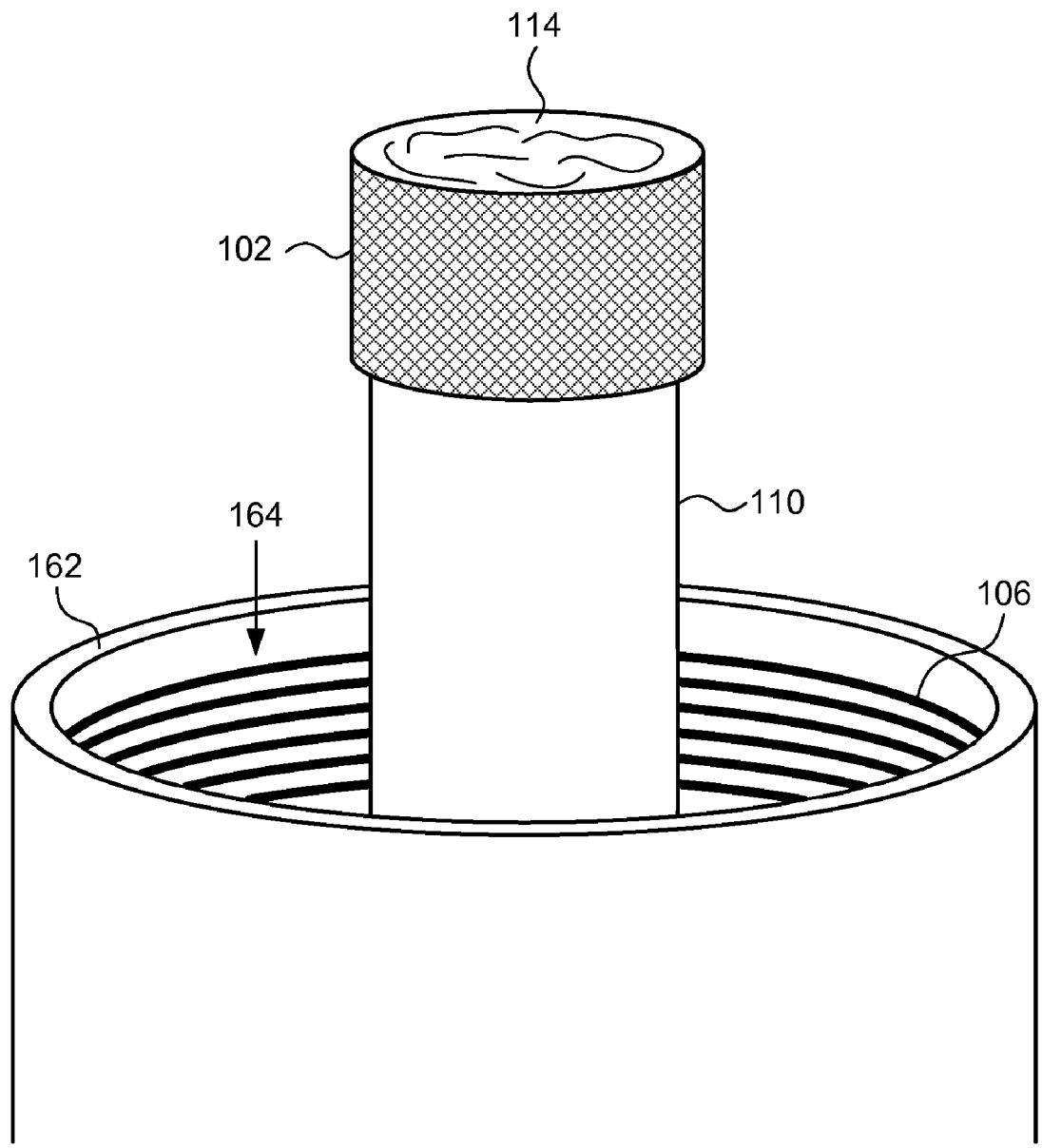
FIG. 11 depicts a schematic diagram of another embodiment of an electrode assembly with a separate ceramic tube to house the heater.

FIG. 11 depicts a schematic diagram of another embodiment of an electrode assembly with a separate ceramic tube 162 to house the heater 106. The depicted embodiment includes the ceramic tube 110, the electrode 102, the braze 114, and the heater 106 within the separate ceramic tube 162. Although not shown, the ceramic tube 110 may use an embodiment of the conductive pin 150, the conductive wire 158, or another conductive medium to transmit signals from the electrode 102, for example, to the electronic controller 130. The heater 106 is disposed within the separate ceramic tube 162, which is offset from the ceramic tube 110 to form an air gap 164 between the heater 106 and the ceramic tube 110. Similar to the air dielectric gap 154 described above, the air gap 164 between the heater 106 and the ceramic tube 110 eliminates or substantially prevents electrical current leakage from the heater 106 through the ceramic tube 106. Since the air gap 164 between the heater 106 and the ceramic tube 110 is on the outside of the ceramic tube 110, some embodiments of the electrode assembly may omit the air dielectric gap 154 inside of the ceramic tube 110, since the air gap 164 outside of the ceramic tube 110 may be sufficient to substantially electrically leakage through the ceramic tube 110 to the conductive element inside the ceramic tube 110.

Figure 12:
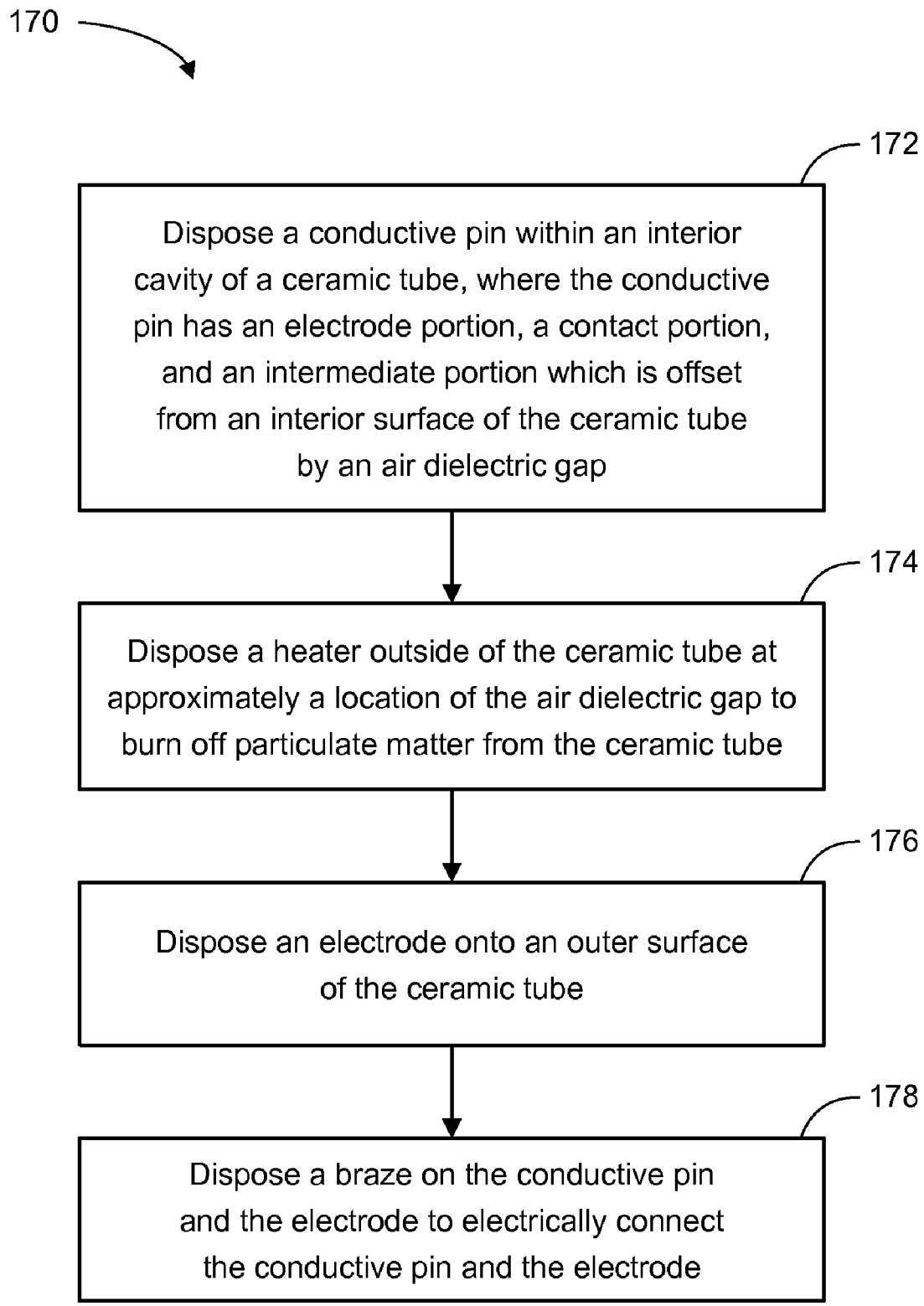
FIG. 12 depicts a flow chart diagram of one embodiment of a method for making an electrode assembly with a conductive pin.

FIG. 12 depicts a flow chart diagram of one embodiment of a method 170 for making an electrode assembly for a sensor. More specifically, the method 170 may be used to make an electrode assembly for the particulate matter sensor 100 using a conductive pin 150. Although the method 170 is described in conjunction with the particulate matter sensor 100 of FIG. 1, other embodiments of the method 170 may be implemented with other particulate matter sensors. Similarly, embodiments of the method 170 may be implemented with a variety of conductive pins having different geometries.

The illustrated method 170 includes disposing 172 a conductive pin 150 within an interior cavity of a ceramic tube 110. The conductive pin 150 includes an electrode portion coupled to an electrode (e.g., the electrode 102) at a first end of the ceramic tube 110. The conductive pin 150 also includes a contact portion at a second end of the ceramic tube 100 for connection to an external conductor 156. The conductive pin 150 also includes an intermediate portion between the electrode portion and the contact portion. The intermediate portion has dimensions that are smaller than the interior cavity of the ceramic tube 110. In this way, as described above, the intermediate portion at least partially defines the air dielectric gap 154 between the intermediate portion and the interior surface of the ceramic tube 110.

The method 170 also includes disposing 174 a heater 106 outside of the ceramic tube 110. The heater 106 can be used to apply heat to the ceramic tube 110 to burn off particulate matter from the ceramic tube 110.

In some embodiments, the method 170 also includes disposing 176 an electrode 102 onto an outer surface of the ceramic tube 110. Alternatively, the electrode may be formed by an exposed surface of the electrode portion of the conductive pin 150.

In an embodiment which includes a separate electrode 102 disposed onto the outer surface of the ceramic tube 110, the method 170 also includes disposing 178 a braze 114 on the conductive pin 150 and the electrode 102 to electrically connect the conductive pin 150 and the electrode 102. Alternatively, if the electrode portion of the conductive pin 150 forms the electrode, the braze 114 may be disposed to mechanically support the conductive pin 150 within the ceramic tube 110, with or without providing electrical conductivity. The depicted method 170 then ends.

Figure 13:
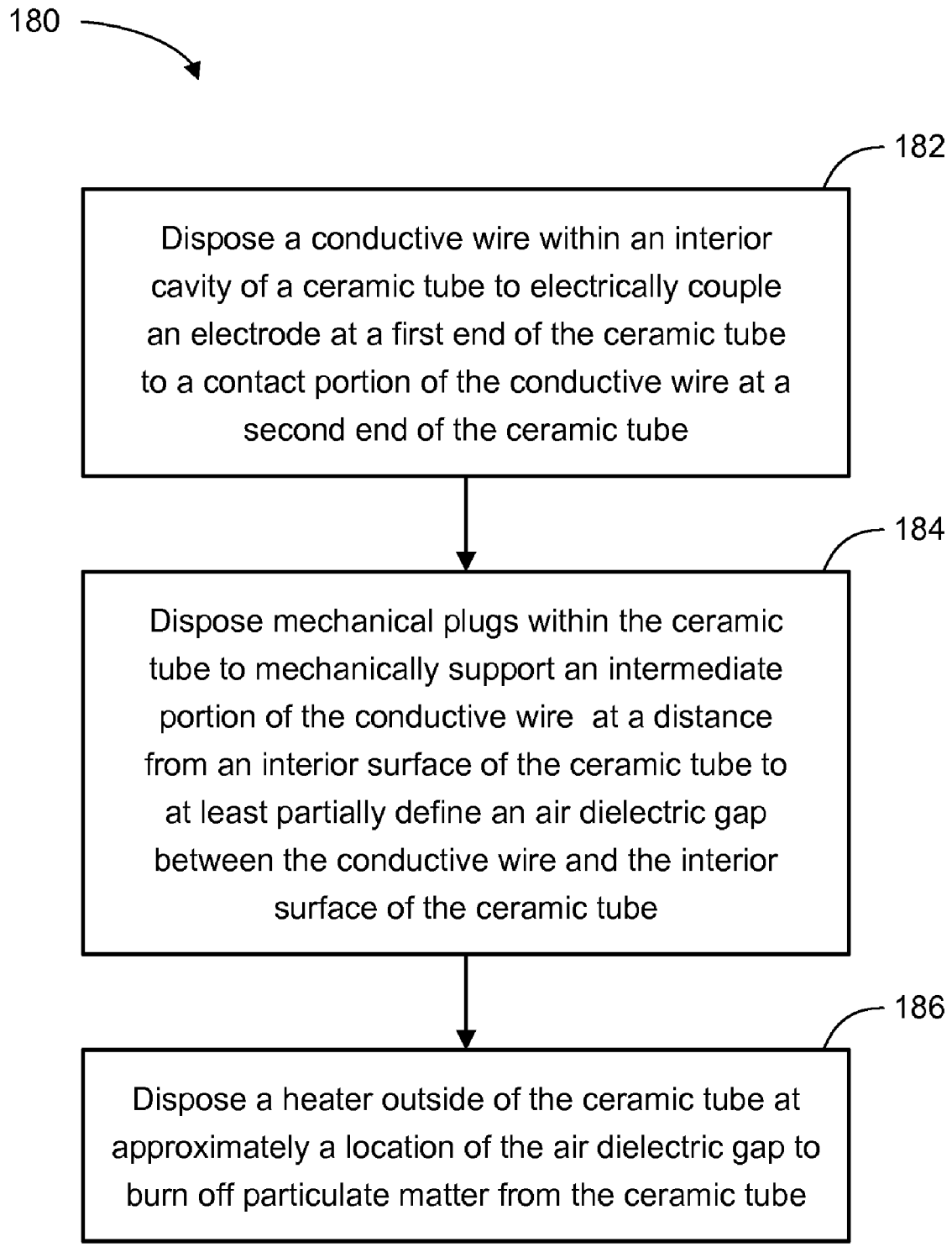
FIG. 13 depicts a flow chart diagram of one embodiment of a method for making an electrode assembly with a conductive wire.

FIG. 13 depicts a flow chart diagram of one embodiment of a method 180 for making an electrode assembly for a sensor. More specifically, the method 180 may be used to make an electrode assembly for the particulate matter sensor 100 using a conductive wire 158. Although the method 180 is described in conjunction with the particulate matter sensor 100 of FIG. 1, other embodiments of the method 180 may be implemented with other particulate matter sensors. Similarly, embodiments of the method 180 may be implemented with a variety of conductive wires 158 and/or mechanical plugs 160 having different geometries.

The illustrated method 180 includes disposing 182 a wire conductor 158 within an interior cavity of a ceramic tube 110. The conductive wire 158 is coupled to the electrode 102 at a first end of the ceramic tube 110. The conductive wire 158 also includes a contact portion at a second end of the ceramic tube 110 for connection to an external conductor 156. The method also includes disposing 184 mechanical plugs 160 within the ceramic tube 110 to mechanically support an intermediate portion of the conductive wire 158 at a distance from the interior surface of the ceramic tube 110. More specifically, the mechanical plugs 160 support the conductive wire 158 at a location to at least partially define an air dielectric gap 154 between the conductive wire 154 and the interior surface of the ceramic tube 110. The method 180 also includes disposing 186 a heater 106 outside of the ceramic tube 110. The heater 106 can be used to apply heat to the ceramic tube 110 to burn off particulate matter from the ceramic tube 110. The depicted method 180 then ends.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

In the above description, specific details of various embodiments are provided. However, some embodiments may be practiced with less than all of these specific details. In other instances, certain methods, procedures, components, structures, and/or functions are described in no more detail than to enable the various embodiments of the invention, for the sake of brevity and clarity.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. An electrode assembly for a particulate matter sensor in a gas environment, the electrode assembly comprising:
   an insulating tube which has an outer surface and defines an interior cavity with an interior surface;
   a conductor disposed within the interior cavity of the insulating tube, the conductor electrically coupled to an electrode at a first end of the insulating tube and comprising a contact portion at a second end of the insulating tube for connection to an external conductor; and
   a positioning structure coupled to the conductor, the positioning structure to mechanically support the conductor at a distance from the interior surface of the insulating tube to at least partially define an air dielectric gap at approximately a heater location corresponding to a heater, wherein the positioning structure has an outer diameter approximately equal to an inner diameter of the insulating tube and has an inner diameter approximately equal to an outer diameter of the conductor.

2. The electrode assembly of claim 1, wherein the conductor has a coefficient of thermal expansion that is substantially equal to a coefficient of thermal expansion of the insulating tube.

3. The electrode assembly of claim 1, wherein the conductor has a coefficient of thermal expansion greater than a coefficient of thermal expansion of the insulating tube.

4. The electrode assembly of claim 1, wherein the conductor comprises a conductive pin, wherein the conductive pin comprises:
   an electrode portion having a shape and size to substantially match dimensions of the interior cavity at the first end of the insulating tube;
   a contact portion having a shape and size to substantially match dimensions of the interior cavity at a second end of the insulating tube; and
   an intermediate portion between the electrode portion and the contact portion, wherein the intermediate portion has a shape and size which are smaller than dimensions of the interior cavity at the location corresponding to the heater to define the air dielectric gap between the intermediate portion of the pin and the interior surface of the insulating tube.

5. The electrode assembly of claim 1, wherein the conductor comprises a conductive wire having a diameter which is substantially smaller than the interior cavity of the insulating tube, wherein positioning structures are positioned at each end of the insulating tube, wherein each positioning structure has an inner diameter approximately equal to the diameter of the conductive wire, wherein each positioning structure is configured to position the conductive wire away from the interior surface of the insulating tube at the location corresponding to the heater to define the air dielectric gap between the conductive wire and the interior surface of the insulating tube.

6. The electrode assembly of claim 1, wherein the electrode assembly further comprises a high temperature braze to mechanically couple the conductor to the insulating tube.

7. The electrode assembly of claim 1, wherein the electrode assembly further comprises a high temperature braze to form an electrical connection with the conductor of the electrode assembly.

8. The electrode assembly of claim 1, wherein the electrode assembly further comprises a high temperature braze to seal the air dielectric gap to prevent particulate matter from entering the air dielectric gap.

9. The electrode assembly of claim 1, further comprising the heater, wherein the heater comprises a resistance heater to burn off an accumulation of particulate matter from the electrode assembly.

10. The electrode assembly of claim 9, wherein the resistance heater comprises a coil of electrically resistive wire disposed outside of the insulating tube.

11. The electrode assembly of claim 9, wherein the heater is printed on the outer surface of the insulating tube.

12. The electrode assembly of claim 9, wherein the heater is recessed at least partially within a groove on the outer surface of the insulating tube.

13. The electrode assembly of claim 9, wherein the heater is disposed in an interior cavity of a separate insulating tube, the separate insulating tube configured to fit approximately around the electrode assembly, wherein an outer air dielectric gap is at least partially defined between the heater and the outer surface of the insulating tube of the sensor assembly.

14. The electrode assembly of claim 9, wherein the positioning structure has a coefficient of thermal expansion substantially equal to a coefficient of thermal expansion of the insulating tube to maintain the conductive pin within the insulating tube of a range of temperatures.

15. The electrode assembly of claim 1, wherein the positioning structure has a coefficient of thermal expansion greater than a coefficient of thermal expansion of the insulating tube to maintain the conductive pin within the insulating tube of a range of temperatures.

16. The electrode assembly of claim 1, wherein the insulating tube comprises a ceramic tube.

17. A system for detecting particulate matter, the system comprising:
a sensor assembly to detect the particulate matter in a gas environment, the sensor assembly comprising:
a pair of insulating tubes;
a conductor disposed within an interior cavity of each insulating tube, each conductor electrically coupled to an electrode at a first end of the corresponding insulating tube and comprising a contact portion at a second end of the corresponding insulating tube for connection to an external conductor, wherein at least a portion of each conductor is offset from the interior surface of the insulating tube by an air dielectric gap at approximately a heater location corresponding to a heater; and
a positioning structure coupled to each conductor, the positioning structure to mechanically support the corresponding conductor at a distance from the interior surface of the corresponding insulating tube to at least partially define the air dielectric gap around the corresponding conductor; and
an electronic controller to determine an amount of the particulate matter within the gas environment.

18. The system of claim 17, wherein the system further comprises:
a detection electrode disposed on a first insulating tube; and
a bias electrode disposed on the second insulating tube, wherein the bias electrode is separated from the detection electrode by an air gap for passage of a portion of a gas stream through the air gap.

19. The system of claim 17, further comprising a plurality of heaters, wherein at least one heater is disposed with respect to each of the first and second insulating tubes, wherein the heaters are configured to apply heat to the first and second insulating tubes to burn off the particulate matter from the first and second insulating tubes.

20. The system of claim 19, wherein the electronic controller is further configured to control a frequency of operation of the heaters.

21. The system of claim 19, wherein the electronic controller is further configured to control a temperature of operation of the heaters.

22. The system of claim 19, wherein each conductor comprises a conductive pin disposed within the interior cavity of the corresponding insulating tube, the conductive pin electrically coupled to an electrode at a first end of the corresponding insulating tube and comprising a contact portion at a second end of the corresponding insulating tube for connection to a corresponding external conductor.

23. The system of claim 17, wherein each conductor comprises a conductive wire disposed within the interior cavity of the corresponding insulating tube, the conductive wire electrically coupled to an electrode at a first end of the corresponding insulating tube and comprising a contact portion at a second end of the corresponding insulating tube for connection to a corresponding external conductor.

24. An electrode assembly for a sensor, the electrode assembly comprising:
an insulating tube which has an outer surface and defines an interior cavity with an interior surface;
a conductive pin disposed within the interior cavity of the insulating tube, the conductive pin comprising:
an electrode portion at a first end of the insulating tube;
a contact portion at a second end of the insulating tube for connection to an external conductor; and
an intermediate portion, between the electrode portion and the contact portion, the intermediate portion having dimensions smaller than the interior cavity of the insulating tube to at least partially define an air dielectric gap between the intermediate portion and the interior surface of the insulating tube.

25. The electrode assembly of claim 24, further comprising an electrode with an exposed surface at the first end of the insulating tube for exposure to a gas stream.

26. The electrode assembly of claim 25, wherein the electrode portion of the conductive pin extends outside of the first end of the insulating tube to form the electrode.

27. The electrode assembly of claim 24, further comprising a braze to electrically connect the electrode portion of the conductive pin to the electrode, wherein the electrode is disposed on the outer surface of the insulating tube.

28. The electrode assembly of claim 24, further comprising a braze at approximately the second end of the insulating tube to mechanically support the conductive pin relative to the insulating tube.

29. The electrode assembly of claim 24, wherein the conductive pin has a coefficient of thermal expansion substantially equal to a coefficient of thermal expansion of the insulating tube to maintain the conductive pin within the insulating tube over a range of temperatures.

30. The electrode assembly of claim 24, wherein the conductive pin has a coefficient of thermal expansion greater than a coefficient of thermal expansion of the insulating tube to maintain the conductive pin within the insulating tube over a range of temperatures.

31. An electrode assembly for a sensor, the electrode assembly comprising:
- a insulating tube which has an outer surface and defines an interior cavity with an interior surface;
- a conductive wire disposed within the interior cavity of the insulating tube, the conductive wire electrically coupled to an electrode at a first end of the insulating tube and comprising a contact portion at a second end of the insulating tube for connection to an external conductor; and
- mechanical plugs coupled to the conductive wire within the insulating tube, the mechanical plugs to mechanically support an intermediate portion of the conductive wire at a distance from the interior surface of the insulating tube to at least partially define an air dielectric gap between the conductive wire and the interior surface of the insulating tube.

32. The electrode assembly of claim 31, wherein the conductive wire extends through a first mechanical plug disposed at the first end of the insulating tube to connect to the electrode at the first end of the insulating tube and extends through a second mechanical plug disposed at the second end of the insulating tube to connect to the external connector.

33. The electrode assembly of claim 32, further comprising a high temperature braze to electrically connect the conductive wire to the electrode.

34. A method for making an electrode assembly for a particulate matter sensor, the method comprising:
- disposing a conductive pin within an interior cavity of an insulating tube, the conductive pin comprising:
  - an electrode portion coupled to an electrode at a first end of the insulating tube;
  - a contact portion at a second end of the insulating tube for connection to an external conductor; and
  - an intermediate portion, between the electrode portion and the contact portion, the intermediate portion having dimensions smaller than the interior cavity of the insulating tube to at least partially define an air dielectric gap between the intermediate portion and an interior surface of the insulating tube; and
- disposing a heater outside of the insulating tube at approximately a location of the air dielectric gap, the heater to apply heat to burn off particulate matter from the insulating tube.

35. The method of claim 34, further comprising applying a braze to the insulating tube and the conductive pin, wherein the braze comprises a high temperature braze.

36. The method of claim 35, further comprising disposing an electrode onto an outer a surface of the insulating tube, wherein the braze electrically connects the conductive pin and the electrode.

37. The method of claim 35, further comprising applying the braze to mechanically support the conductive pin within the insulating tube.

38. The method of claim 34, wherein the electrode portion of the conductive pin extends outside of the first end of the insulating tube to form the electrode.

39. The method of claim 34, wherein disposing the heater further comprises at least partially recessing the heater within a groove on an outer surface of the insulating tube.

40. The method of claim 34, further comprising disposing the heater in an interior cavity of a separate insulating tube around the insulating tube in which the conductive pin is disposed, wherein an outer air dielectric gap is at least partially defined between the heater and the outer surface of the insulating tube.

41. A method for making an electrode assembly for a particulate matter sensor, the method comprising:
- disposing a conductive wire within an interior cavity of an insulating tube, the conductive wire electrically coupled to an electrode at a first end of the insulating tube and comprising a contact portion at a second end of the insulating tube for connection to an external conductor;
- disposing mechanical plugs coupled to the conductive wire within the insulating tube, the mechanical plugs to mechanically support an intermediate portion of the conductive wire at a distance from an interior surface of the insulating tube to at least partially define an air dielectric gap between the conductive wire and the interior surface of the insulating tube; and
- disposing a heater outside of the insulating tube at approximately a location of the air dielectric gap, the heater to apply heat to burn off particulate matter from the insulating tube.

42. The method of claim 41, further comprising applying a braze to the insulating tube and the conductive wire, wherein the braze comprises a high temperature braze.

43. The method of claim 42, further comprising disposing an electrode onto an outer a surface of the insulating tube, wherein the braze electrically connects the conductive wire and the electrode.

44. The method of claim 42, further comprising applying the braze to mechanically support at least one of the mechanical plugs within the insulating tube.

45. The method of claim 41, wherein disposing the heater further comprises at least partially recessing the heater within a groove on an outer surface of the insulating tube.

46. The method of claim 41, further comprising disposing the heater in an interior cavity of a separate insulating tube around the insulating tube in which the conductive wire is disposed, wherein an outer air dielectric gap is at least partially defined between the heater and the outer surface of the insulating tube.

* * * * *